US012629339B2

(12) United States Patent
Gaudana et al.

(10) Patent No.: US 12,629,339 B2
(45) Date of Patent: *May 19, 2026

(54) LITHIUM SALT EXTENDED-RELEASE FORMULATIONS; METHODS OF MAKING; AND METHODS OF USE THEREOF

(71) Applicant: Almatica Pharma LLC, Morristown, NJ (US)

(72) Inventors: Ripal Gaudana, Morristown, NJ (US); Raghav Gupta, Morristown, NJ (US); Rama Yarasani, Morristown, NJ (US)

(73) Assignee: ALMATICA PHARMA LLC, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/379,854

(22) Filed: Nov. 5, 2025

(65) Prior Publication Data

US 2026/0060933 A1 Mar. 5, 2026

Related U.S. Application Data

(63) Continuation of application No. 18/751,410, filed on Jun. 24, 2024.

(60) Provisional application No. 63/522,883, filed on Jun. 23, 2023.

(51) Int. Cl.
A61K 9/20 (2006.01)
A61K 33/00 (2006.01)

(52) U.S. Cl.
CPC .......... *A61K 9/2077* (2013.01); *A61K 9/2031* (2013.01); *A61K 9/2054* (2013.01); *A61K 9/2086* (2013.01); *A61K 33/00* (2013.01)

(58) Field of Classification Search
CPC .. A61K 9/2077; A61K 9/2031; A61K 9/2054; A61K 9/2086; A61K 33/00
See application file for complete search history.

(56) References Cited

U.S. PATENT DOCUMENTS

2024/0423919 A1 12/2024 Gaudana et al.

OTHER PUBLICATIONS

Damasio, Lithium Carbonate and Cluster Headaches; pp. 1-8; J. Neurol. 224 (Year: 1980).*
Souza, Film Coating, BioMed Res. Intl. (Year: 2014).*
Aurelie, L. et al.; "External Evaluation of Population Pharmacokinetics Models of Lithium in the Bipolar Population"; Pharmaceuticals, vol. 16, 1627; 15 pages; DOI: 10.3390/ph16111627 (2023).
Beal, S.; "Ways to Fit a PK Model with Some Data Below the Quantification Limit"; Journal of Pharmacokinetics and Pharmacodynamics, vol. 28, Issue No. 5; pp. 481-504 (2001).

Lithium Carbonate Extended-Release Tablets USP, 450 mg (Hikma Pharmaceuticals USA Inc., Revised: Jun. 2023).
Findling, R. et al.; "First-Dose Pharmacokinetics of Lithium Carbonate in Children and Adolescents"; J Clin Psychopharmacol, Author manuscript; available in PMC Aug. 1, 2011; 17 pages.
Goo, R.H. et al.; "Circadian Variation in Gastric Emptying of Meals in Humans"; Gastroenterology, vol. 93; pp. 515-518 (1987).
Itoh, M. et al.; "Lithium carbonate-induced Stevens-Johnson syndrome: the first case report"; International Journal of Dermatology, vol. 62; pp. e165-e167 (2023).
Jeppsson and Sjogren; "The Influence of Food on Side Effects and Absorption of Lithium"; vol. 51; pp. 285-288 (1975).
Jin, Z-B. et al.; "Population Pharmacokinetics and Dosing Regimen of Lithium in Chinese Patients with Bipolar Disorders"; Frontiers in Pharmacology, vol. 13, Article 913935; DOI: 10.3389/fphar.2022. 913935 (2022); 8 pages.
Landersdorfer, C. et al.; "Lithium in Paediatric Patients with Bipolar Disorder: Implications for Selection of Dosage Regimens via Population Pharmacokinetics/Pharmacodynamics"; Clin Pharmacokinet, 56(1); DOI:10.1007/s40262-016-0430-3 (2016); 14 pages.
Lithium Carbonate 300 mg tablet; 150 mg, 300 mg, and 600 mg capsule [Prescribing Information]; Berkeley Heights, NJ, USA; Hikma Pharmaceuticals USA Inc.; 45 pages (revised Nov. 2022).
Lithium Carbonate; Draft Guidance on Lithium Carbonate [Prescribing Information]; available online at "www.fda.gov/regulatory-information/search-fda-guidance-documents"; 3 pages (revised May 2023).
Seo, J. and Mittal, R.; "Computational Modeling of Drug Dissolution in the Human Stomach"; Frontiers in Physiology, vol. 12, Article No. 755997; 14 pages; DOI: 10.3389/fphys.2021.755997 (2022).
Van Rongen, A. et al.; "Population Pharmacokinetic Model Characterizing 24-Hour Variation in the Pharmacokinetics of Oral and Intravenous Midazolam in Healthy Volunteers"; CPT Pharmacometrics Syst Pharmacol, vol. 4; pp. 454-464; DOI:10.1002/psp4.12007 (2015).
Yu, W. et al.; "Population Pharmacokinetics of Lithium Carbonate in Young Male Healthy Chinese Volunteers"; Pharmacopsychiatry, DOI http://dx.doi.org/10.1055/s-0042-103329 (Published online 2016); 5 pages.
Barr Laboratories_Lithium Carbonate_Prntlbl 2002, 8 pages.
DOW Brochure "Using METHOCEL Cellulose Ethers for Controlled Release of Drugs in Hydrophilic Matrix Systems" Published Jul. 2000, 36 pages.
ESKALITH CR Prescribing Information Sep. 2003, 8 pages.
Hikma Lithium Carbonate Extended-Release Tablets Prescribing Information Revised Oct. 2022_Label revised Jun. 2023, 12 pages.
LITHOBID Label Oct. 2022, 10 pages.
Hwang, K-M. et al.; "Swellable and porous bilayer tablet for gastroretentive drug delivery: Preparation and in vitro-in vivo evaluation"; Int J Pharmaceutics, vol. 572, 118783; 13 pages; DOI: 10.1016/j.ijpharm.2019.118783 (2019).
U.S. Appl. No. 19/442,284, filed Jan. 7, 2026 Inventors Ripal Gaudana, Raghav Gupta, Rama Yarasani; Applicant: Almatica Pharma LLC; Title: Lithium Salt Extended-Release Formulations; Methods of Making; and Methodsof Use Thereof.

* cited by examiner

*Primary Examiner* — Sarah Alawadi
*Assistant Examiner* — Thurman Wheeler
(74) *Attorney, Agent, or Firm* — CANTOR COLBURN LLP

(57) ABSTRACT

Disclosed are high dose gastric retentive, extended-release lithium salt dosage forms suitable for once a day administration.

5 Claims, No Drawings

LITHIUM SALT EXTENDED-RELEASE FORMULATIONS; METHODS OF MAKING; AND METHODS OF USE THEREOF

CROSS-REFERENCE TO RELATED APPLICATIONS

This application is a continuation of U.S. patent application Ser. No. 18/751,410, filed Jun. 24, 2024, which claims the benefit of U.S. Provisional Application No. 63/522,883, filed Jun. 23, 2023, each of which is hereby incorporated by reference in its entirety for all purposes.

BACKGROUND

Lithium carbonate was originally approved in the United States (U.S.) in 1970 as a 300 mg oral capsule. Other solid oral dosage forms of immediate-release lithium carbonate (i.e., tablets) as well as an oral syrup (as lithium citrate) have also been approved and marketed in the U.S. Extended-release lithium carbonate products have been approved in the U.S., including ESKALITH CR® (450 mg lithium carbonate extended-release tablet; NDA 018152; discontinued), LITHOBID® (300 mg lithium carbonate extended-release tablet; NDA 018027). LITHOBID and the ANDA-approved 450 mg lithium carbonate extended-release tablet product marketed by Hikma Pharmaceuticals USA Inc. (ANDA 076691).

Lithium is recognized as having a narrow therapeutic index (NTI) (Drug Bank DBCAT003972), and the prescribing information for lithium carbonate products marketed in the U.S. carry a Black Box Warning regarding lithium toxicity being closely related to serum lithium levels and which can occur at doses close to therapeutic levels. The therapeutic range for lithium is identified as 0.8-1.2 mEq/L and the toxic concentration of lithium is understood to be ≥1.5 mEq/L.

Currently for treatment of acute mania 1800 mg of lithium carbonate per day is prescribed and the same is achieved by administering 3 tablets of LITHOBID® ER 300 mg in the morning and 3 tablets in the evening. Thus, patients need to take 6 tablets, while for long term control, 900-1200 mg/day is required. Again, this requires administration of multiple tablets as well as twice daily dosing using currently approved products. Using the 450 mg extended-release tablet also requires multiple tablets and twice daily dosing to achieve 900 mg and greater strengths required for either long term control or acute mania. Due to lithium having a NTI, close monitoring of patients serum level lithium is required and the existing immediate release formulations are prescribed for closer titration.

Therefore, there remains a need in the art for a higher strength lithium salt formulation that exhibits an extended-release profile for reduced number of administrations per day with fewer dosage units per administration for simpler and more convenient dosing.

SUMMARY

Disclosed herein is an extended-release oral tablet, comprising an extended-release polymer matrix portion comprising lithium carbonate and a controlled-release polymer; and a gastroretentive portion comprising a swellable polymer; wherein the tablet contains greater than 450 mg lithium carbonate per tablet. In an embodiment, the tablet is in the form of a layered tablet comprising a first layer comprising the extended-release polymer matrix portion and a second layer comprising the gastroretentive portion. In an embodiment, the tablet comprises 900 mg lithium carbonate.

In another embodiment, a method of preparing an extended-release tablet comprises providing a first blend comprising lithium carbonate and a controlled-release polymer; providing a second blend comprising a swellable polymer; and compressing the first blend and the second blend to form a bilayer tablet comprising greater than 450 mg lithium carbonate per tablet. In an embodiment, the tablet comprises 900 mg lithium carbonate.

In another embodiment, a method of treating a subject in need thereof comprises administering the tablet described herein to a subject in need thereof to treat depression or mania.

The above described and other features are exemplified by the following detailed description.

DETAILED DESCRIPTION

Disclosed herein are higher strength, extended-release oral lithium salt formulations that require fewer doses per day than immediate release or currently available extended release tablet formulations, which require multiple doses per day. The formulation satisfies an unmet medical need for a once a day oral lithium dosage form and would greatly benefit patients currently taking multiple tablets twice a day. Patient compliance is improved with a reduced number of administrations and reduced pill burden.

In an embodiment, the lithium salt is lithium carbonate and the formulation is a gastroretentive, extended release tablet formulation providing therapeutic lithium levels for 24 hours. It has been found that a layered tablet comprising a first layer comprising the extended-release polymer matrix portion and a second layer comprising the gastroretentive portion advantageously provides 24 hour extended release due to the absorption window of lithium. A single layer extended release/gastroretentive formulation did not work well as it slows down the dissolution. A single layer extended release/non gastroretentive formulation does not work well as it exits the absorption window for lithium prematurely. The layered tablet comprising a first layer comprising the extended-release polymer matrix portion and a second layer comprising the gastroretentive portion provides the necessary retention and release profile required for a 24 hour dosing.

An extended-release oral tablet comprises an extended-release polymer matrix portion comprising lithium carbonate and a controlled-release polymer; and a gastroretentive portion comprising a swellable polymer, wherein the tablet contains greater than 450 mg lithium carbonate per tablet. Specifically, the tablet contains about 500 mg or more of lithium carbonate per tablet, about 600 mg or more of lithium carbonate, about 700 mg or more of lithium carbonate, about 800 mg or more of lithium carbonate, or about 900 mg lithium carbonate per tablet.

The extended-release polymer matrix portion comprising lithium carbonate and a controlled-release polymer provides extended release of lithium through erosion and diffusion. The gastroretentive portion comprises a swellable polymer that swells and promotes gastroretention of the dosage form in the stomach. This allows the dosage form to remain longer within its optimum absorption window in the gastrointestinal tract, thereby providing better absorption of the active. The use of the gastroretentive portion allows for the dosage form to remain in the stomach for a longer duration of time than a corresponding dosage form without the gastroretentive portion. The extended time in the stomach allows for the lithium to be fully released and to get absorbed completely.

The gastroretentive portion can be formulated to tailor the degree of retention in the stomach by adjusting size of the portion, type and amount of swellable polymer (average weight, size), use of different excipients, etc. The gastroretentive portion and swellable polymers are selected to provide rapid swelling while exhibiting enough gel strength to withstand the fed stomach conditions.

By "once-a-day administration" is meant administration once within a 24 hour period.

In certain embodiments, the extended-release polymer matrix portion of the extended-release oral tablet comprises lithium carbonate and a controlled-release polymer, wherein the lithium carbonate can be present in an amount of about 60 to about 90 weight percent (wt %) based on the total weight of the extended-release polymer matrix portion, specifically about 65 to about 85 wt %, and yet more specifically about 70 to about 80 wt %.

Suitable controlled-release polymers for use in the extended-release polymer matrix portion include hydroxypropyl methyl cellulose, including high molecular weight hydroxypropyl methyl cellulose having a molecular weight of about 4,000 to about 1,500,000, or 25,000 and above. Suitable commercially available controlled-release grades of hydroxypropyl methyl cellulose include those available from Colorcon and International Flavors and Fragrances Inc., specifically the METHOCEL Premium CR Grades (see Table 1). A single controlled-release grade of hydroxypropyl methyl cellulose can be used, or a combination of hydroxypropyl methyl cellulose of varying grades can be used (e.g., combination of METHOCEL K4M CR and K100 LV, or K15M CR and K100 LV).

4

TABLE 2

| Grade | Approximate Molecular Weight[1] | Viscosity of aqueous solution at 25° C. and given concentration, | |
|---|---|---|---|
| | | Wt % | mPa · s (cP) |
| POLYOX ™ WSR N-10 | 100,000 | 5 | 12-50 |
| POLYOX ™ WSR N-80 | 200,000 | 5 | 65-115 |
| POLYOX ™ WSR N-750 | 300,000 | 5 | 600-1,000 |
| POLYOX ™ WSR N-3000 | 400,000 | 5 | 2,250-4,500 |
| POLYOX ™ WSR 205 | 600,000 | 5 | 4,500-8,800 |
| POLYOX ™ WSR 1105 | 900,000 | 5 | 8,800-17,600 |
| POLYOX ™ WSR N-12K | 1,000,000 | 2 | 400-800 |
| POLYOX ™ WSR N-60K | 2,000,000 | 2 | 2,000-4,000 |
| POLYOX ™ WSR 301 | 4,000,000 | 1 | 1,650-5,500 |
| POLYOX ™ WSR Coagulant | 5,000,000 | 1 | 5,500-7,500 |
| POLYOX ™ WSR 303 | 7,000,000 | 1 | 7,500-10,000 |
| POLYOX ™ WSR 308 | 8,000,000 | 1 | 10,000-15,000 |
| UCARFLOC ™ Polymer 304 CP[2] | 7,500,000 | 1 | 7,500-13,000 |
| UCARFLOC ™ Polymer 309 CP[2] | 8,500,000 | 1 | >13,000 |

[1]Based on rheological measurements. Molecular weights obtained by other methods, including light scattering and gel permeation chromatography, may not be directly comparable.
[2]Coarse Particle (CP) grade specified as less than 15% through a 200 mesh screen (74 μm).

The controlled-release polymer or combination of controlled-release polymers can be present in the extended-release polymer matrix portion in an amount of about 8 to about 40 wt % based on the total weight of the extended-release polymer matrix portion, specifically about 10 to about 30 wt %, and yet more specifically about 12 to about 20 wt %.

TABLE 1

| | METHOCEL Premium Product Grade | | | | | |
|---|---|---|---|---|---|---|
| | K100 Premium LV CR | K4M Premium CR | K15M Premium CR | K100M Premium CR | E4M Premium CR | E10M Premium CR |
| Methoxyl, % (USP) | 19-24 | 19-24 | 19-24 | 19-24 | 28-30 | 28-30 |
| Hydroxypropoxyl, % (USP) | 7-12 | 7-12 | 7-12 | 7-12 | 7-12 | 7-12 |
| Substitution type (USP/EP) | 2208 | 2208 | 2208 | 2208 | 2910 | 2910 |
| Apparent viscosity, 2% in water at 20° C., cP (USP) | 80-120 | 3000-5600 | 11250-21000 | 80000-120000 | 3000-5600 | 7500-14000 |
| Apparent viscosity, 2% in water at 20° C., mPa · s (EP) | 78-117 [98 Nom] | 2308-3755 [2903 Nom] | 6138-9030 [7382 Nom] | 16922-19267 [18243 Nom] | 2308-3755 [2903 Nom] | 4646-7070 [5673 Nom] |

The controlled-release polymer for use in the extended-release polymer matrix portion may also be a high molecular weight polyethylene oxide having an approximate molecular weight of 100,000 or greater based on dilute viscosity measurements, specifically about 200,000, about 300,000, about 400,000, about 600,000, about 900,000, about 1,000,000, about 2,000,000, about 4,000,000, about 5,000,000, about 7,000,000, etc. Exemplary swellable polymers for use in the extended release portion include the nonionic polyethylene oxide polymers sold under the name POLYOX™ WSR (Water-Soluble Resins) and the polyethylene oxide polymers sold under the name UCARFLOC™ Polymer in Table 2.

The tablet comprises a gastroretentive portion responsible for extensive swelling to promote retention of the dosage form in the stomach allowing the lithium to be released fully and to get absorbed completely. The gastroretentive portion is formulated to result in fast swelling while exhibiting enough gel strength to withstand the fed stomach conditions and allow sufficient gastric retention for complete absorption of the lithium salt.

The swellable polymer for use in the gastroretentive portion of the dosage form may be any suitable water-swellable or water-soluble polymer including a high molecular weight polyethylene oxide; a cellulose ether such as a hydroxypropyl methyl cellulose, hydroxypropyl cellulose, hydroxyethyl cellulose, and the like; a cellulose such as ethyl cellulose, methyl cellulose, sodium carboxy methyl cellulose; a carbomer (acrylic acid polymer); acacia; pectin; agar; gellan gum; guar gum; an alginate or alginic acid; acrylic acid derivatives such as polycarbophil (acrylic acid polymer crosslinked with divinyl glycol), and the like; chitosan; a combination thereof, and the like.

The swellable polymer may be a high molecular weight polyethylene oxide having an approximate molecular weight of 100,000 or greater based on dilute viscosity measurements, specifically about 200,000, about 300,000, about 400,000, about 600,000, about 900,000, about 1,000,000, about 2,000,000, about 4,000,000, about 5,000,000, about 7,000,000, etc. Exemplary swellable polymers for use in the gastroretentive portion include the POLYOX WSR polymers.

The swellable polymer or combination of swellable polymers make up the bulk of the gastroretentive portion. The swellable polymer can be present in the gastroretentive portion in an amount of greater than about 50 wt % and up to 100 wt % by weight of the gastroretentive portion, specifically about 75 to about 99.5 wt %, and more specifically about 85 to about 99 wt %.

The gastroretentive portion can further comprise a gas generating agent. Exemplary gas generating agents include a carbonate source including carbonate and bicarbonate salts. Suitable carbonate sources include an alkali or alkaline earth metal carbonate, an alkali or alkaline earth metal hydrogen carbonate, a combination thereof, and the like. In an embodiment, the gas generating agent is sodium hydrogen carbonate.

The gastroretentive portion can further comprise an excipient to promote rapid hydration such as a disintegrant (e.g., crospovidone), a channel forming agent (e.g. Eudragit® EPO), a combination thereof, and the like. Exemplary channel forming agents include a cationic copolymer based on dimethylaminoethyl methacrylate, butyl methacrylate, and methyl methacrylate random copolymer. These cationic copolymers are referred to as Amino Methacrylate Copolymer—NF according to USP/NF (United States Pharmacopeia (USP) and the National Formulary (NF)), Basic Butylated Methacrylate Copolymer of European Pharmacopoeia (Ph. Eur.), and Aminoalkyl Methacrylate Copolymer E of Japanese Pharmacopoeia (JPE). Commercially available cationic copolymer based on dimethylaminoethyl methacrylate, butyl methacrylate, and methyl methacrylate includes Evonik Industries' Eudragit® EPO, Eudragit® E 100, Eudragit® E 12,5, or a combination thereof having a ratio of dimethylaminoethyl methacrylate, butyl methacrylate, and methyl methacrylate of 2:1:1.

The tablets may further comprise one or more suitable tablet excipients, such as a binder, a filler, a lubricant, a glidant, a colorant, a disintegrant, or any combination thereof. The one or more suitable tablet excipients may be present in the extended-release polymer matrix portion, the gastroretentive portion, or both. In certain embodiments, the tablet excipient can be an intragranular ingredient with the active agent, an extragranular ingredient blended with active agent granules, or a combination thereof.

Suitable binders for use in the tablets include polyvinylpyrrolidone; a cellulosic polymer including hydroxypropyl cellulose, hydroxyethyl cellulose, methylcellulose, ethyl cellulose, and the like; gum Arabic; alginic acid and its derivatives; a sugar or sugar alcohol such as mannitol, lactose, and the like; a starch; or a combination thereof. In certain embodiments, the binder is an intragranular ingredient. In one aspect, the binder is polyvinylpyrrolidone.

Suitable disintegrants include crospovidone, croscarmellose sodium, sodium starch glycolate, a starch, or a combination thereof.

Suitable fillers include a water insoluble filler, such as dicalcium phosphate, starch, powdered cellulose, microcrystalline cellulose, and the like. Exemplary water-soluble fillers include water soluble sugars and sugar alcohols, specifically lactose, glucose, fructose, sucrose, mannose, dextrose, galactose, mannitol, sorbitol, xylitol, and the like. Combinations of fillers may be used. In certain embodiments, the filler is an intragranular ingredient. In certain embodiments, the filler is an extragranular ingredient.

Exemplary lubricants include talc, calcium stearate, magnesium stearate, solid polyethylene glycols, sodium lauryl sulfate, glyceryl behenate, a combination thereof, and the like. In one aspect, the lubricant is magnesium stearate.

Exemplary glidants include colloidal silicon dioxide, starch, talc, a combination thereof, and the like.

In certain embodiments, the gastroretentive portion is substantially free or free of a lithium salt. As used herein, substantially free of a lithium salt means the gastroretentive portion contains less than 10 wt %, specifically less than 5 wt %, and more specifically less than 1 wt % of a lithium salt based on the total weight of the gastroretentive portion.

The weight ratio of the extended-release polymer matrix portion to the gastroretentive portion can be about 5:1 to about 1:1, specifically about 4.5:1 to about 1.5:1, more specifically about 4:1 to about 2:1, yet more specifically about 3.5:1 to about 2.5:1, and still yet more specifically about 3:1.

The tablet formulations herein may optionally further comprise a non-controlled-release coating, that is, an immediate-release coating, a color-identifying coating, a cosmetic coating, a seal coating, or the like. The non-controlled-release coating, optionally referred to as a non-functional coating, should not have an impact on the release of the active agent due to the initial dissolution, hydration, perforation of the coating, etc., and would not be considered to be a significant deviation from the non-coated formulation. Suitable non-controlled-release coating materials include immediate release film coating systems commercially available by COLORCON under the name OPADRY. Non-controlled-release coatings can include a water-soluble polymer, plasticizer, and optionally a pigment or colorant.

In an embodiment, the extended-release tablet is not an effervescent formulation and does not comprise an effervescent or gas generating component.

The extended-release oral tablets can be administered once daily to a subject in need thereof to treat depression or mania. In an embodiment, the extended-release oral tablets can be administered once daily with food or in the fed state to a subject in need thereof to treat depression or mania. When administered with food, the tablet can be administered at the same time as the consumption of food, substantially at the same time as the food, or within about 30 minutes before or after the food, specifically about 20 minutes, more specifically about 15 minutes, yet more specifically about 10 minutes, and still yet more specifically about 5 minutes before or after the food. In further embodiments, the tablet can be administered at the same time as the consumption of food, substantially at the same time as the food, or within about 30 minutes after the food, specifically about 20 minutes, more specifically about 15 minutes, yet more specifically about 10 minutes, and still yet more specifically about 5 minutes after the food "Food" typically means a solid food or mixed solid/liquid food with sufficient bulk and fat content that it is not rapidly dissolved and absorbed in the stomach. In a further embodiment, the food is a high fat meal, high calorie meal, or high fat and high calorie meal.

A "high fat" meal generally means about 30% or more of the total caloric content of the meal is fat, specifically about 40% or more, and yet more specifically about 50% or more. A "high calorie" meal means a meal of about 600 to about 1200 calories, more specifically about 800 to about 1000 calories. In an embodiment, the food is a high-fat and high-calorie meal described as a test meal for food-effect bioavailability and fed bioequivalence studies as set out in the U.S. Food and Drug Administration's Guidance for Industry, Food-Effect Bioavailability and Fed Bioequivalence Studies, U.S. Department of Health and Human Services, Food and Drug Administration, Center for Drug Evaluation and Research (CDER), December 2002. The test meal can derive approximately 150, 250, and 500-600 calories from protein, carbohydrate, and fat, respectively. An example test meal according to the Guidance would be two eggs fried in butter, two strips of bacon, two slices of toast with butter, four ounces of hash brown potatoes and eight ounces of whole milk. Substitutions of this test meal can be made with a meal that provides a similar amount of calories from protein, carbohydrate, and fat and has comparable meal volume and viscosity.

In an embodiment, the administration of the tablets in the fed state results in enhanced bioavailability of the lithium salt compared to in the fasted state. In an embodiment, the administration of the tablets in the fed state results in an increase in $C_{max}$, $AUC_{0-t}$, $AUC_{0-\infty}$, or a combination thereof compared to in the fasted state. The area under the plasma concentration-time curve from time zero to the time of measurement of the last quantifiable concentration ($AUC_{0-t}$) and to infinity ($AUC_{0-\infty}$), peak plasma concentration ($C_{max}$), and time to peak concentration ($T_{max}$) can be determined according to standard techniques.

The features and advantages are more fully shown by the following examples, which are provided for purposes of illustration and are not to be construed as limiting the invention in any way.

EXAMPLES

Example 1. Extended-Release Lithium Carbonate Matrix Tablet (Non Gastro-Retentive)

| Example 1. | |
| --- | --- |
| Component | % |
| Lithium carbonate | 71.4 |
| Povidone | 3.0 |
| Microcrystalline cellulose (AVICEL PH 101) | 12.7 |
| Hypromellose (HPMC K15M Premium CR) | 6.0 |
| Hypromellose (HPMC K100LV CR) | 5.6 |
| Colloidal silicon dioxide (Cab-O-Sil, M5P) | 0.5 |
| Magnesium stearate | 0.8 |

Povidone binder solution was prepared in purified water. Lithium carbonate (API), some part of microcrystalline cellulose and hypromellose (HPMC K15M Premium CR) were mixed in High-Shear Mixer (GMX) for dry mixing and granulated using the povidone binder solution. Then the granulation was dried using fluid bed dryer until the loss on drying (LOD) was less than or equal to 1%. The dried granulation was milled through Fitzmill. The milled granulation was blended with extra-granular materials such as remaining microcrystalline cellulose, hypromellose (K100 LV CR), colloidal silicon dioxide. The blend was lubricated using magnesium stearate using the same blender. Finally, single layer tablets were compressed using rotary tablet press as per target tablet weight. The core tablets were then film-coated using an Opadry II film coating.

Examples 2-5. Extended-Release Lithium Carbonate Matrix Bilayer Tablet-Gastroretentive Formulation

| | Example 2. | Example 3. | Example 4. | Example 5. |
| --- | --- | --- | --- | --- |
| | | % | | |
| API Granules | | | | |
| Lithium carbonate | 58.3 | 61.9 | 62.5 | 62.5 |
| Povidone | 2.3 | 2.5 | 2.5 | 2.5 |
| Extended release Blend | | | | |
| Microcrystalline cellulose (AVICEL PH 101) | 3.9 | — | 4.2 | 4.2 |
| Polyethylene oxide (WSR 205 grade) | — | 8.3 | — | — |
| Hypromellose (HPMC K4M Premium CR) | 7.8 | 2.1 | 6.3 | 8.3 |
| Hypromellose (HPMC K 100 LV) | 3.6 | — | — | 0.0 |
| Hypromellose (HPMC K100 Premium LV CR) | — | — | 5.9 | 3.8 |
| Colloidal silicon dioxide | 0.3 | — | 0.3 | 0.3 |
| Magnesium stearate | 0.6 | 0.6 | 0.7 | 0.7 |
| Gastroretentive Layer | 0.0 | 0.0 | 0.0 | 0.0 |
| Polyethylene oxide (WSR 303) | 18.2 | 19.3 | 6.9 | 6.9 |
| Hypromellose (Methocel K15M Premium) | 4.8 | 5.0 | 1.9 | 1.9 |
| Crospovidone (Type A) | — | — | 2.4 | 2.4 |
| Sodium Bicarbonate | — | — | 3.0 | 3.0 |
| Carbomer Homopolymer Type A, (Carbopol 71G) | 0.0 | 0.0 | 3.2 | 3.2 |
| Colorant | 0.1 | 0.1 | 0.1 | 0.1 |
| Magnesium stearate | 0.3 | 0.3 | 0.2 | 0.2 |

Lithium carbonate has been granulated using aqueous povidone solution in a High-Shear Mixer (GMX). The granules were dried using fluid bed dryer until the LOD was less than or equal to 1% was achieved. The dried granulation was milled through a Fitzmill obtain API granules.

The API granules were blended with extra-granular materials and then lubricated using magnesium stearate using a blender to obtain the API layer blend. This final blend was used in the compression of manufacturing of the bilayer tablet as the API layer.

The placebo layer blend was prepared by blending the placebo layer materials and the blend was lubricated using magnesium stearate in a blender to obtain the placebo layer blend. This final blend was used in the compression of manufacturing of the bilayer tablet as the placebo layer.

The API layer blend and placebo layer blend were compressed using a rotary tablet press to obtain bilayer tablets with target hardness of approximately 20 kp. The bilayer tablet cores could then be film-coated using Opadry to obtain film coated bilayer tablets.

Example 6. Dissolution Study

The extended-release lithium carbonate matrix tablet (non gastroretentive) of Example 1 was analyzed in a dissolution study utilizing USP Apparatus 1 (Baskets) at 100 rpm in pH 4.5 acetate buffer (900 mL; 37.0° C.±0.5° C.) as dissolution medium. Dissolution samples were collected at 2, 4, 6, 8, 10, 12, 14, 16, 20 and 24 hours and analyzed with HPLC employing conductivity detection by comparing the peak response in the samples to that of a standard solution with known concentration of lithium. The mean dissolution data are provided in the table below, along with the dissolution results for a comparative 450 mg lithium carbonate extended-release tablet product (ANDA 076691 Hikma Pharmaceuticals USA Inc).

| Time (hr) | Lithium Carbonate Tablet, 450 mg | Example 1 Lithium Carbonate Tablet, 900 mg |
|---|---|---|
| | % released | |
| 2 | 44 | 23 |
| 4 | 68 | 48 |
| 6 | 84 | 70 |
| 8 | 95 | 88 |
| 10 | 101 | 98 |
| 12 | 100 | 102 |
| 14 | 100 | 103 |
| 16 | 99 | 102 |
| 20 | 99 | 102 |
| 24 | 99 | 102 |

Example 7. Dissolution Study

The extended-release lithium carbonate matrix bilayer tablets (gastro-retentive) of Examples 2-5 were analyzed in a dissolution study utilizing USP Apparatus 3 (Reciprocating Cylinder) at 20 dips per minute (DPM) in pH 4.5 acetate buffer (250 mL; 37.0° C.±0.5° C.) as dissolution medium. Dissolution samples were collected at 0.5, 1, 2, 3, 4, 6, 8, 10 and 12 hours and analyzed with HPLC employing conductivity detection by comparing the peak response in the samples to that of a standard solution with known concentration of lithium. The mean dissolution data are provided in the table below, along with the dissolution results for a comparative 450 mg lithium carbonate extended-release tablet product (ANDA 076691 Hikma Pharmaceuticals USA Inc).

| Time (hr) | Lithium Carbonate Tablet, 450 mg | Lithium Carbonate Tablet, 900 mg | | | |
|---|---|---|---|---|---|
| | | Example 2 | Example 3 | Example 4 | Example 5 |
| | | % released | | | |
| 0.5 | 34 | 17 | 19 | 11 | 11 |
| 1 | 60 | 20 | 35 | 24 | 21 |
| 2 | 96 | 45 | 63 | 49 | 42 |
| 3 | 105 | 61 | 81 | 64 | 58 |
| 4 | 107 | 76 | 90 | 75 | 74 |
| 6 | 106 | 88 | 95 | 82 | 80 |
| 8 | 106 | 92 | 101 | 89 | 85 |
| 10 | 106 | 98 | 102 | 94 | 89 |
| 12 | 106 | 100 | 103 | 100 | 93 |

Examples 2-5 are gastroretentive bilayer tablet formulations. It is expected that the placebo layer will swell and promote gastric retention, while the API layer continues to release lithium carbonate by erosion and diffusion. Using the gastroretentive formulation, it is expected that all of the lithium carbonate is released within the absorption window to allow for a complete absorption of lithium into the system of the subject.

Examples 8-10. Extended-Release Lithium Carbonate Matrix Tablet (Non Gastroretentive) and Matrix Bilayer (Gastroretentive) Tablets

| Example 8. | |
|---|---|
| Granulation | % |
| Lithium carbonate | 69.7 |
| Povidone | 2.9 |
| Microcrystalline cellulose (AVICEL PH 101) | 12.4 |
| Hypromellose (HPMC K100LV CR) | 5.4 |
| Hypromellose (HPMC K15M Premium) | 5.8 |
| Colloidal silicon dioxide (Cab-O-Sil, M5P) | 0.5 |
| Magnesium stearate | 0.8 |
| Film coating | 2.4 |
| Purified water | — |

Example 8 lithium carbonate matrix tablets were prepared in a similar process to Example 1; the intragranular ingredients included povidone, lithium carbonate (API), and microcrystalline cellulose. The granules were dried to LOD of less than or equal to 1.5% to form Lithium carbonate Granules. The Lithium carbonate Granules were blended with extragranular ingredients microcrystalline cellulose, the hypromellose ingredients, colloidal silicon dioxide, and magnesium stearate. Single layer tablets were compressed using rotary tablet press as per target tablet weight. The core tablets were then film-coated using an Opadry II film coating.

| | Example 9. | Example 10. |
| | | % |
|---|---|---|
| API Granules | | |
| Lithium carbonate | 55.9 | 59.3 |
| Povidone | 2.2 | 2.4 |
| Extended release Blend | | |
| Microcrystalline cellulose (AVICEL PH 101) | 2.5 | — |
| Polyethylene oxide (WSRN12K LEO) | — | 9.9 |
| Hypromellose (HPMC K4M Premium CR) | 8.1 | — |
| Hypromellose (HPMC K100 Premium LV CR) | 4.0 | — |
| Colloidal silicon dioxide | 0.2 | — |
| Magnesium stearate | 0.6 | 0.5 |
| Gastroretentive Layer | | |
| Polyethylene oxide (WSR 303) | 19.4 | 20.6 |
| Hypromellose (Methocel K15M Premium) | 5.1 | 5.4 |
| Colorant | 0.04 | 0.05 |
| Magnesium stearate | 0.3 | 0.3 |
| Total Placebo Layer | 24.9 | 26.4 |
| Film coating | 1.5 | 1.5 |
| Purified water | — | — |

Examples 9.-10. Extended-Release Lithium Carbonate Matrix Bilayer Tablet, Gastroretentive Formulations were Prepared by Processes Similar to Examples 2.-5

Example 11. Bioavailability Studies, Fed State

Bioavailability studies in the fed state were conducted for the tablets of Examples 8-10. Open label, balanced, single oral dose, randomized, four-period, four-treatment, four sequence, crossover, relative bioavailability study of test formulations of Examples 8-10 (Lithium Carbonate Extended Release Tablets 900 mg) administered once a day compared to Reference formulation Lithium Carbonate Extended-Release Tablets, 450 mg (Hikma Pharmaceuticals USA Inc.) administered twice a day in healthy adult human subjects under fed conditions. The results of the studies are provided in the following Tables. Example 9 once a day extended-release tablet was found to be bioequivalent to currently available 450 mg Lithium Carbonate Extended-Release Tablets twice a day, thereby providing a high strength lithium salt formulation with a satisfactory extended-release profile for reduced number of administrations per day and fewer dosage units per administration for simpler and more convenient dosing. Key benefits of once-a-day formulation include low peak and trough drug concentration or spikes due to single time dosing compared to twice daily dosing. Since the pill burden will reduce to half, the once a day extended-release tablet would significantly enhance patient compliance and treatment adherence.

For Example 8 (T) vs. Reference (R):

| | Geometric Least Squares Means and its ratio | | | | |
|---|---|---|---|---|---|
| PK Parameters (Units) | Test Product (T) (N = 16) | Reference Product (R) (N = 16) | (T/R) (%) | Intra-subject CV (%) | 90% Confidence Interval |
| $C_{max}$ (ng/mL) | 5357.987 | 3490.536 | 153.50 | 15.32 | 139.23%-169.23% |

-continued

| | Geometric Least Squares Means and its ratio | | | | |
|---|---|---|---|---|---|
| PK Parameters (Units) | Test Product (T) (N = 16) | Reference Product (R) (N = 16) | (T/R) (%) | Intra-subject CV (%) | 90% Confidence Interval |
| $AUC_{0-t}$ (hr * ng/mL) | 97193.989 | 109741.432 | 88.57 | 13.33 | 81.35%-96.42% |
| $AUC_{0-\infty}$ (hr * ng/mL) | 101876.634 | 115779.877 | 87.99 | 12.78 | 81.10%-95.47% |

For Example 9 (T) vs. Reference (R):

| | Geometric Least Squares Means and its ratio | | | | |
|---|---|---|---|---|---|
| PK Parameters (Units) | Test Product (T) (N = 15) | Reference Product (R) (N = 15) | (T/R) (%) | Intra-subject CV (%) | 90% Confidence Interval |
| $C_{max}$ (ng/mL) | 3613.434 | 3456.896 | 104.53 | 14.41 | 95.19%-114.79% |
| $AUC_{0-t}$ (hr * ng/mL) | 106745.753 | 109638.895 | 97.36 | 5.39 | 93.99%-100.85% |
| $AUC_{0-\infty}$ (hr * ng/mL) | 111717.543 | 115580.325 | 96.66 | 4.95 | 93.58%-99.83% |

For Example 10 (T) vs. Reference (R):

| | Geometric Least Squares Means and its ratio | | | | |
|---|---|---|---|---|---|
| PK Parameters (Units) | Test Product (T) (N = 14) | Reference Product (R) (N = 14) | (T/R) (%) | Intra-subject CV (%) | 90% Confidence Interval |
| $C_{max}$ (ng/mL) | 3016.836 | 3576.811 | 84.34 | 18.40 | 74.20%-95.87% |
| $AUC_{0-t}$ (hr * ng/mL) | 96821.306 | 110167.633 | 87.89 | 31.38 | 70.88%-108.98% |
| $AUC_{0-\infty}$ (hr * ng/mL) | 102109.342 | 116583.882 | 87.58 | 31.23 | 70.70%-108.50% |

Example 12. Bioavailability Studies, Fasting State

Bioavailability studies in the fasting state were conducted for the tablets of Examples 9-10. Open label, balanced, single oral dose, randomized, three-period, three-treatment, three sequence, three-way crossover, relative bioavailability study of test formulations of Examples 9-10 (Lithium Carbonate Extended Release Tablets 900 mg) administered once a day compared to Reference formulation Lithium Carbonate Extended-Release Tablets, 450 mg (Hikma Pharmaceuticals USA Inc.) administered twice a day in healthy adult human subjects under fasting conditions. The results of the studies are provided in the following Tables.

For Example 9 (T) vs. Reference (R):

| PK Parameters (Units) | Geometric Least Squares Means and its ratio | | | | |
|---|---|---|---|---|---|
| | Test Product (T) (N = 16) | Reference Product (N = 16) | (T/R) (%) | Intra-subject CV (%) | 90% Confidence Interval |
| $C_{max}$ (ng/mL) | 2233.460 | 3662.617 | 60.98 | 16.54 | 55.00%-67.61% |
| $AUC_{0-t}$ (hr * ng/mL) | 46854.920 | 107193.177 | 43.71 | 22.80 | 37.95%-50.35% |
| $AUC_{0-\infty}$ (hr * ng/mL) | 48838.310 | 111563.679 | 43.78 | 22.32 | 38.11%-50.28% |

For Example 10 (T) vs. Reference (R):

| PK Parameters (Units) | Geometric Least Squares Means and its ratio | | | | |
|---|---|---|---|---|---|
| | Test Product (T) (N = 15) | Reference Product (N = 15) | (T/R) (%) | Intra-subject CV (%) | 90% Confidence Interval |
| $C_{max}$ (ng/mL) | 2281.435 | 3644.095 | 62.61 | 9.54 | 58.80%-66.66% |
| $AUC_{0-t}$ (hr * ng/mL) | 49546.344 | 104351.474 | 47.48 | 17.88 | 42.23%-53.38% |
| $AUC_{0-\infty}$ (hr * ng/mL) | 51500.718 | 108497.299 | 47.47 | 17.71 | 42.27%-53.30% |

A bioavailability study in the fasting state was conducted for the single layer tablet of Example 8. Open label, balanced, single oral dose, randomized, four-period, four-treatment, four sequence, crossover, relative bioavailability study of test formulation of Example 8 (Lithium Carbonate Extended Release Tablets 900 mg) administered once a day compared to Reference formulation Lithium Carbonate Extended-Release Tablets, 450 mg (Hikma Pharmaceuticals USA Inc.) administered twice a day in healthy adult human subjects under fasting conditions. The results of the study are provided in the following Table.

For Example 8 (T) vs. Reference (R):

| PK Parameters (Units) | Geometric Least Squares Means and its ratio | | | | |
|---|---|---|---|---|---|
| | Test Product (T) (N = 22) | Reference Product (R) (N = 22) | (T/R) (%) | Intra-subject CV (%) | 90% Confidence Interval |
| $C_{max}$ (ng/mL) | 4413.7 | 3977.0 | 110.98 | 11.85 | 104.29%-118.09% |
| $AUC_{0-t}$ (hr * ng/mL) | 95539.0 | 120604.0 | 79.22 | 18.70 | 71.86%-87.33% |
| $AUC_{0-\infty}$ (hr * ng/mL) | 100534.5 | 127211.7 | 79.03 | 18.77 | 71.66%-87.16% |

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

In general, the disclosure may alternately comprise, consist of, or consist essentially of, any appropriate components herein disclosed. The disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The endpoints of all ranges directed to the same component or property are inclusive of the endpoints, are independently combinable, and include all intermediate points and ranges (e.g., ranges of "up to 25 wt %, or more specifically 5 to 20 wt %" is inclusive of the endpoints and all intermediate values of the ranges of "5 to 25 wt %," such as "10 to 23 wt %," "20 to 24," "1 to 5 wt %," etc.). Disclosure of a narrower range or more specific group in addition to a broader range is not a disclaimer of the broader range or larger group.

"Combination" is inclusive of blends, mixtures, reaction products, and the like.

The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

Unless otherwise specified herein, any reference to standards, regulations, testing methods and the like, refer to the standard, regulation, guidance or method that is in force at the time of filing of the present application.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. An extended-release, bilayer oral tablet, comprising:
a.) a first layer comprising an extended-release polymer matrix portion comprising
about 70 to about 80 wt % lithium carbonate,
about 10 to about 20 wt % of a hydroxypropyl methyl cellulose, polyvinylpyrrolidone,
microcrystalline cellulose, and
a glidant, a lubricant, or a glidant and a lubricant,
wherein the weight percents of lithium carbonate and hydroxypropyl methyl cellulose are based on the total weight of the extended-release polymer matrix portion;
b.) a second layer comprising a gastroretentive portion comprising about 75 to about 85 wt % of a swellable polymer based on the total weight of the gastroretentive portion, wherein the swellable polymer is a high molecular weight polyethylene oxide having a molecular weight of 100,000 grams per mole or greater,

a hydroxypropyl methyl cellulose, and
a lubricant, a colorant, or a lubricant and a colorant; and
c.) a film coating;
wherein the tablet contains about 600 mg lithium carbonate per tablet and a weight ratio of the extended-release polymer matrix portion to the gastroretentive portion is about 2.5:1 to about 1.5:1; or
wherein the tablet contains about 900 mg lithium carbonate per tablet and a weight ratio of the extended-release polymer matrix portion to the gastroretentive portion is about 3.5:1 to about 2.5:1.

2. The tablet of claim 1, wherein the tablet contains about 600 mg lithium carbonate.

3. The tablet of claim 1, wherein the tablet contains about 900 mg lithium carbonate.

4. A method of treating a subject in need thereof, comprising: administering the tablet of claim 1 once daily to the subject to treat depression or mania.

5. A method of treating a subject in need thereof, comprising: administering the tablet of claim 1 once daily with food to the subject to treat depression or mania.

* * * * *